(12) United States Patent
Watanabe

(10) Patent No.: US 6,727,266 B2
(45) Date of Patent: Apr. 27, 2004

(54) SUBSTITUTED TRYPTOPHAN DERIVATIVES

(75) Inventor: Fumihiko Watanabe, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/169,836

(22) PCT Filed: Jan. 23, 2001

(86) PCT No.: PCT/JP01/00412
§ 371 (c)(1), (2), (4) Date: Jul. 10, 2002

(87) PCT Pub. No.: WO01/55133
PCT Pub. Date: Aug. 2, 2001

(65) Prior Publication Data
US 2003/0130325 A1 Jul. 10, 2003

(30) Foreign Application Priority Data
Jan. 26, 2000 (JP) .................................. 2000-016370

(51) Int. Cl.⁷ .................. A61K 31/41; A61P 19/02; C07D 409/12
(52) U.S. Cl. .................. 514/364; 514/414; 548/143; 548/253; 548/467
(58) Field of Search ................. 548/467, 143, 548/253; 514/414, 364, 381

(56) References Cited
FOREIGN PATENT DOCUMENTS

| WO | 97/27174 A1 | 7/1997 |
|---|---|---|
| WO | 99/4780 A1 | 2/1999 |
| WO | 2000/63194 A1 | 1/2000 |
| WO | WO 0015213 * | 3/2000 |
| WO | 2000/15213 A1 | 3/2000 |

\* cited by examiner

*Primary Examiner*—Robert W. Ramsuer
*Assistant Examiner*—Robert Shiao
(74) *Attorney, Agent, or Firm*—Birch, Stewart, Kolasch & Birch, LLP

(57) ABSTRACT

A compound of the formula (I):

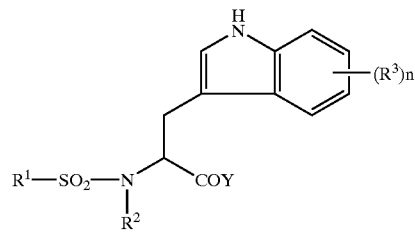

wherein: $R^1$ is represented by the formula:

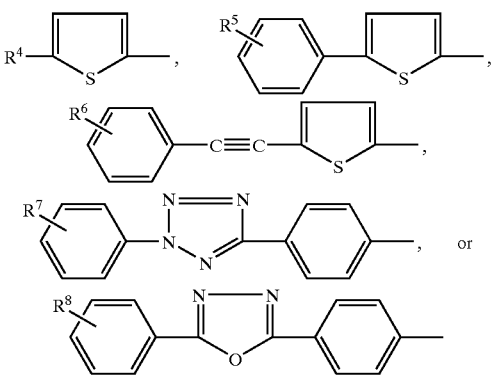

wherein $R^4$, $R^5$, $R^6$, $R^7$ and $R^8$ are monovalent radicals such as: hydrogen, halogen, optionally substituted lower alkyl, lower alkyloxy, lower alkylthio, optionally substituted amino, nitro; non-aromatic heterocyclic group, and the like with certain provisos;

Y is —OH or —NHOH;

$R^2$ is hydrogen, optionally substituted lower alkyl, or optionally substituted aralkyl;

$R^3$ is halogen, hydroxy, lower alkyloxy, or lower alkylthio;

(b) n is an integer from 1 to 3;

its optically active substance, its prodrug, its pharmaceutically acceptable salt, and its solvate.

13 Claims, No Drawings

SUBSTITUTED TRYPTOPHAN DERIVATIVES

This application is the national phase under 35 U.S.C. § 371 of PCT International Application No. PCT/JP01/00412 which has an International filing date of Jan. 23, 2001, which designated the United States of America.

TECHNICAL FIELD

This invention relates to substituted tryptophane derivatives and metalloproteinase inhibitors containing the same.

BACKGROUND ART

An extracellular matrix, consisting of collagen, fibronectin, laminin, proteoglycan, etc., has a function to support tissues, and plays a role in propagation, differentiation, adhesion, or the like in cells. Metalloproteinases which are protease having a metal ion in the active center, especially matrix metalloproteinases (MMP), are concerned with the degradation of the extracellular matrix. Many types of MMP, from MMP-1 (type-I collagenase) to MMP-18, have been reported as enzymes working for the growth, remodeling of tissues, etc. under usual physiological conditions. It is reported, however, that the progression of various kinds of diseases involving breakdown and fibrosis of tissues (e.g., osteoarthritis, rheumatoid arthritis, corneal ulceration, periodontitis, metastasis and invasion of tumor, and virus infection (HIV infection)) is related with increase of the manifestation or activity of the above-mentioned enzyme.

Substituted tryptophane derivatives having MMP inhibitory activities are described in WO97/27174, WO99/04780, JP11-246527A, EP-0877018A1 and the like.

DISCLOSURE OF INVENTION

The inventors of the present invention have found that certain new substituted tryptophane derivatives have a potent activity to inhibit MMP.

The present invention relates to 1) a compound of the formula (I):

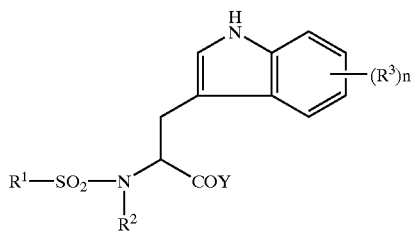

wherein $R^2$ is hydrogen, optionally substituted lower alkyl, or optionally substituted aralkyl;
$R^3$ is halogen, hydroxy, lower alkyloxy, or lower alkylthio;
n is an integer from 1 to 3;
$R^1$ is represented by the formula:

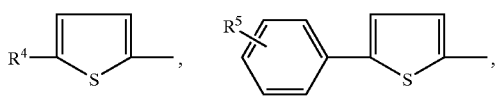

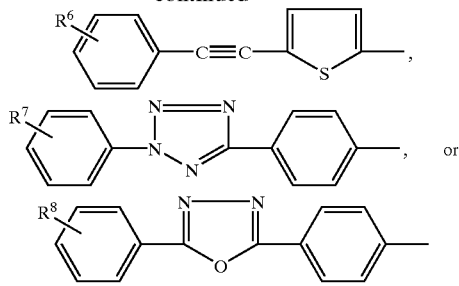

wherein $R^4$ is hydrogen, halogen, optionally substituted lower alkyl, lower alkyloxy, lower alkylthio, optionally substituted amino, or nitro;
$R^5$ is hydrogen, halogen, optionally substituted lower alkyl, lower alkyloxy, lower alkylthio, optionally substituted amino, nitro, or a non-aromatic heterocyclic group, provided that when $R^5$ is amino substituted with two lower alkyls, $R^3$ is not 6- methyloxy or 5-fluoro;
$R^6$ is hydrogen, halogen, optionally substituted lower alkyl, lower alkyloxy, lower alkylthio, optionally substituted amino, or nitro,
provided that when $R^6$ is lower alkyl, $R^3$ is not 6-hydroxy or 6-lower alkyloxy;
$R^7$ is halogen, optionally substituted lower alkyl, lower alkyloxy, lower alkylthio, optionally substituted amino, or nitro;
$R^8$ is hydrogen, halogen, optionally substituted lower alkyl, lower alkyloxy, lower alkylthio, optionally substituted amino, or nitro; and
Y is —OH or —NHOH,
its optically active substance, its prodrug, its pharmaceutically acceptable salt, or its solvate.

In more detail, the invention relates to the following 2) to 12).

2) A compound of 1), wherein $R^1$ is a group represented by the formula:

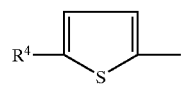

wherein $R^4$ is halogen,
its optically active substance, its prodrug, its pharmaceutically acceptable salt, or its solvate.

3) A compound of 1), wherein $R^1$ is a group represented by the formula:

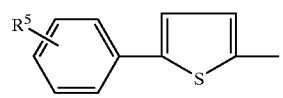

wherein $R^5$ is optionally substituted amino or a non-aromatic heterocyclic group, provided that when $R^5$ is amino substituted with two lower alkyls, $R^3$ is not 6-methyloxy or 5-fluoro;
its optically active substance, its prodrug, its pharmaceutically acceptable salt, or its solvate.

4) A compound of 1), wherein $R^1$ is a group represented by the formula:

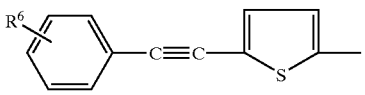

wherein $R^6$ is lower alkyl,
its optically active substance, its prodrug, its pharmaceutically acceptable salt, or its solvate.

5) A compound of 1), wherein $R^1$ is a group represented by the formula:

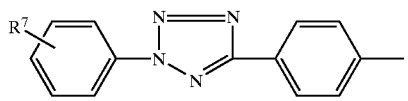

wherein $R^7$ is lower alkyloxy,
its optically active substance, its prodrug, its pharmaceutically acceptable salt, or its solvate.

6) A compound of 1), wherein $R^1$ is a group represented by the formula:

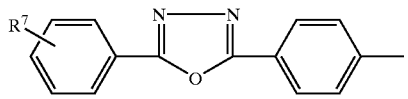

wherein $R^8$ is halogen,
its optically active substance, its prodrug, its pharmaceutically acceptable salt, or its solvate.

7) A compound of any one of 1) to 6), wherein $R^2$ is hydrogen, its optically active substance, its prodrug, its pharmaceutically acceptable salt, or its solvate.

8) A compound of any one of 1) to 7), wherein $R^3$ is halogen, hydroxy, or lower alkyloxy and n is 1, its optically active substance, its prodrug, its pharmaceutically acceptable salt, or its solvate.

9) A pharmaceutical composition containing a compound of any one of 1) to 8) as an active ingredient.

10) A composition for inhibiting matrix metalloproteinase containing a compound of any of 1) to 8) as an active ingredient.

11) Use of a compound of any one of 1) to 8) for preparation of a pharmaceutical composition for treating a disease related with matrix metalloproteinase.

12) A method for treating a disease related with matrix metalloproteinase of a mammal, including a human, which comprises administration to said mammal of a compound of any one of 1) to 8) in a pharmaceutically effective amount.

The term "halogen" herein used means fluoro, chloro, bromo, and iodo. Fluoro, chloro, and bromo are preferred.

In the present specification, the term "lower alkyl" employed alone or in combination with other terms means a straight- or branched chain monovalent hydrocarbon group having 1 to 8 carbon atom(s). Examples of the alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. C1 to C6 alkyl is preferred. C1 to C3 alkyl is more preferred.

In the present specification, the term "aryl" employed alone or in combination with other terms includes monocyclic or condensed ring aromatic hydrocarbons. Phenyl, 1-naphtyl, 2-naphtyl, anthryl, and the like are exemplified.

The term "aralkyl" herein used means the above mentioned "lower alkyl" substituted with the above mentioned one or more "aryl" at any possible position. Examples of the aralkyl are benzyl, phenethyl (e.g., 2-phenethyl and the like), phenylpropyl (e.g., 3-phenylpropyl and the like), naphthylmethyl (e.g., 1-naphthylmethyl and 2-naphthylmethyl and the like), anthrylmethyl (e.g., 9-anthrylmethyl and the like), and the like. Benzyl and phenylethy are preferred.

In the present specification, the term "non-aromatic heterocyclic group" employed alone or in combination with other terms includes a 5 to 7 membered non-aromatic ring which contains one or more hetero atoms selected from the group consisting of oxygen, sulfur, and nitrogen atoms in the ring and a condensed ring which are formed with two or more of the non-aromatic ring. Examples of the non-aromatic heterocyclic group are pyrrolidinyl (e.g., 1-pyrrolidinyl, 2-pyrrolidinyl), imidazolidinyl (e.g., 2-imidazolidinyl), pyrazolidinyl (e.g., 1-pyrazolidinyl, 2-pyrazolidinyl), pyrazolinyl (e.g., pyrazolinyl), piperidyl (piperidino, 2-piperidyl), piperazinyl (e.g., 1-piperazinyl), isoindolynyl (e.g., isoindolynyl), morpholinyl (e.g., morpholino, 3-morpholinyl) and the like.

The term "lower alkyloxy" herein used are methyloxy, ethyloxy, n-propyloxy, isopropyloxy, n-butyloxy, isobutyloxy, sec-butyloxy, tert-butyloxy, and the like. Methyloxy, ethyloxy, n-propyloxy, isopropyloxy and n-butyloxy are preferred.

The term "lower alkylthio" herein used are methylthio, ethylthio, and the like.

In the present specification, the term "acyl" employed alone or in combination with other terms includes alkylcarbonyl in which alkyl group is the above-mentioned "lower alkyl" and arylcarbonyl in which aryl group is the above-mentioned "aryl". Examples of the acyl are acetyl, propionyl, butyloyl, benzoyl, and the like. "Lower alkyl" and "aryl" may be substituted respectively with substituents mentioned below.

In the present specification, the term "optionally substituted amino" employed alone or in combination with other terms includes amino which may be substituted with one or two of the above mentioned "lower alkyl", "aryl", "aralkyl", or "acyl". Examples of the optionally substituted amino are amino, methylamino, dimethylamino, ethylmethylamino, diethylamino, ethylmethylamino, benzylamino, acetylamino, benzoylamino and the like. Preferable are amino, methylamino, dimethylamino, ethylmethylamino, diethylamino and acetylamino.

The substituents of "optionally substituted lower alkyl" herein used are hydroxy, lower alkyloxy, mercapto, lower alkylthio, halogen, nitro, cyano, carboxy, lower alkyloxycarbonyl, optionally substituted amino, acyl, acyloxy, aryloxy (e.g., phenyloxy), aralkyloxy (e.g., benzyloxy), lower alkylsulfonyl, guanidino, an azo group, and the like. These substituents are able to locate at one or more of any possible positions.

BEST MODE FOR CARRYING OUT THE INVENTION

Compounds (I) of the invention are able to be synthesized in accordance with the procedure described in WO97/27174 and the like. 4-substituted or 7-substituted tryptophane derivative as a starting material can be synthesized in accordance with the method described in Tetrahedron Lett. 1989, 39, 4703. 5-substituted tryptophane derivative can be synthesized in accordance with the method described in Chem. Pharm. Bull. 1984, 32, 2126 and 6-substituted tryptophane derivative can be synthesized in accordance with the method described in Chem. Pharm. Bull. 1984, 32, 2544.

The term "solvate" includes, for example, solvates with organic solvents, hydrates, and the like.

The term "compound of the present invention" herein used includes a pharmaceutically acceptable salt or solvate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, mallein acid, fumaric acid, benzenesulfonic acid, p-toluenesulfonic acid, and the like). These salts can be formed by the usual method. The hydrates may coordinate with an arbitrary number of water molecules.

Prodrug is a derivative of the compound of the present invention having a group which can be decomposed chemically or metabolically, and such prodrug is converted to a pharmaceutically active compound of the present invention by means of solvolysis or by placing the compound in vivo under a physiological condition. The selection method and the process method of an appropriate prodrug derivative are described in the literature such as Design of Prodrugs, Elsevier, Amsterdam 1985. When the compounds of the present invention have a carboxyl group, an ester derivative prepared by reacting a basal acid compound with a suitable alcohol or an amide prepared by reacting a basal acid compound with a suitable amine are exemplified as prodrugs. Particularly preferred esters as prodrugs are methyl ester, ethyl ester, n-propyl ester, isopropyl ester, n-butyl ester, isobutyl ester, tert-butyl ester, morpholinoethyl ester, N,N-diethylglycolamido ester, and the like. When the compounds of the present invention have a hydroxy group, an acyloxy derivative prepared by reacting with a suitable acyl halide or a suitable acid anhydride are exemplified as prodrugs. Particularly preferred acyloxy derivatives as prodrugs are —OCOC$_2$H$_5$, —OCO$^t$—Bu, —OCOC$_{15}$H$_{31}$, —OCO(m-COONa—Ph), —OCOCH$_2$CH$_2$COONa, —OCOCH(NH$_2$)CH$_3$, and —OCOCH$_2$N(CH$_3$)$_2$, and the like. When the compounds of the present invention have an amino group, an amide derivative prepared by reacting with a suitable acid halide or a suitable acid anhydride are exemplified as prodrugs. Particularly preferred amide derivatives as prodrugs are —NHCO(CH$_2$)$_{20}$CH$_3$ and —NHCOCH(NH$_2$)CH$_3$, and the like.

The compound of the present invention has an excellent activity for inhibiting MMP and inhibits matrix dissolution, as described in the following test example.

Definitely, the compounds of the present invention are useful in the prevention or treatment of diseases such as osteoarthritis, rheumatoid arthritis, corneal ulceration, periodontal disease, advanced virus infection (e.g., HIV), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis (glomerulopathy), neurodegengerative disease, inflammation, osteoporosis, deossification, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, heart failure, asthmatic respiratory tract disease, arteriosclerosis, and gastric ulcer.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 1 to 20 mg/kg/day for adult.

The following examples are provided to further illustrate the present invention and are not to be constructed as limiting the scope thereof.

Abbreviations described below are used in the following examples.
Me: methyl
Ac: acetyl
DMF: N,N-dimethylformamide

EXAMPLES

Example 1

The preparation of the Compound (A-1)

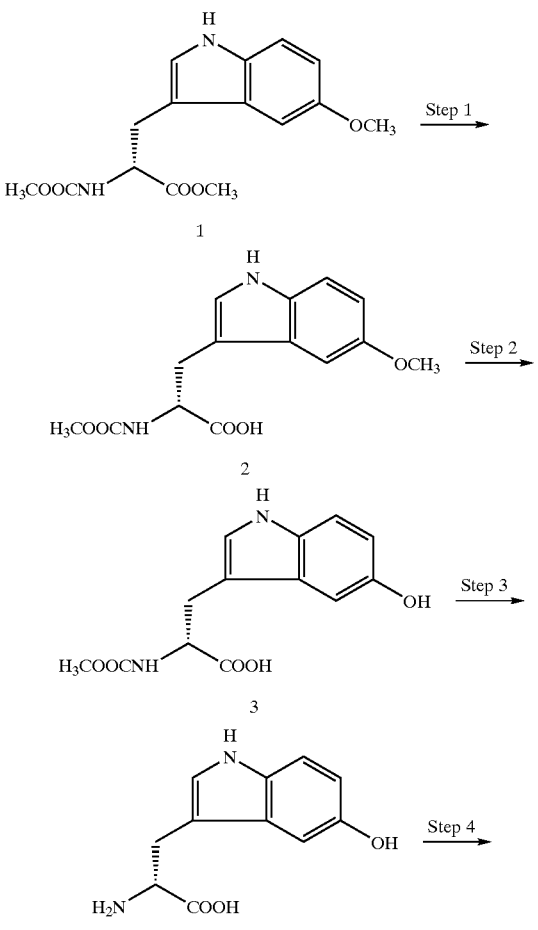

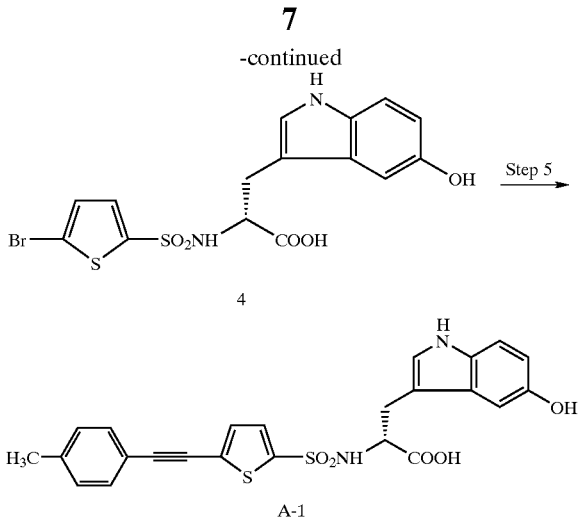

4

A-1

(Step 1)

The starting material (1) was synthesized in accordance with the method described in K Irie et. al., Chem. Pharm. Bull. 1984, 32, 2126. The compound (1) (7 g, 22.9 mmol) was disolved in 140 ml of tetrahydrofuran and to the mixture were added 1 mol/L NaOH (46 mL) and MeOH (28 mL) at ice-cooling. The reaction mixture was stirred for 80 min and poured into 2 mol/L HCl (40 mL). The mixture was extracted with ethylacetate (100 mL×2). The organic layer was washed with water (50 mL) and brine (50 mL), deried over $Na_2SO_4$, and concentrated in vacuo to give 7.34 g of pale brown amorphous.

$^1$H-NMR (DMSO-$d_6$) δ 3.04 (m, 2H), 3.48 (s, 3H), 3.76 (s, 3H), 4.19 (m, 1H), 6.71 (dd, J=2.1, 8.7 Hz, 1H), 7.02 (d, J=2.1 Hz, 1H), 7.11 (d, J=8.4 Hz, 1H), 7.22 (d, J=8.4 Hz, 1H), 7.39 (d, J=8.1 Hz, 1H), 10.67 (s, 1H), 12.5 (br s, 1H).

Mass(m/e)[M+H]$^+$293.

(Step 2)

The compound (2) synthesized in the above step (7.3 g) was suspended in 140 mL of methylene chloride and the suspension was cooled at −70° C. (in a dry ice-acetone bath) under nitrogen. To the mixture was added boron tribromide (1M $CH_2Cl_2$ solution, 69 mL) dropwise over 23 min. After the dry ice-acetone bath was replaced with an ice bath, and the mixture was stirred for 3.5 h. The mixture was poured into iced 2 mol/L HCl (200 mL) and salt was added to the resulting mixture. The mixture was extracted with ethyl acetate (400 mL and 200 mL). The organic layer was washed with brine (200 mL×2), dried over $Na_2SO_4$, and concentrated in vacuo to give 6.75 g of yellow amorphous. According to the $^1$H-NMR spectrum, the obtained amorphous included 17% of the starting material (2) but was used in the next step wihtout purification.

$^1$H-NMR (DMSO-$d_6$) δ 2.95 (m, 2H), 3.48 (s, 3H), 4.16 (m, 1H), 6.58 (dd, J=2.4, 8.7 Hz, 1H), 6.83 (d, J=2.1 Hz, 1H), 7.04 (s, 1H), 7.12 (d, J=8.7 Hz, 1H), 7.36 (d, J=7.8 Hz, 1H), 8.6 (s, 1H), 12.6 (br s, 1H).

Mass(m/e)[M+H]$^+$279.

(Step 3)

The compound (3) synthesized in the above step (2.9 g) was disolved in 30 mL of acetonitrile. To the solution was added trimethylsilyl iodide (4.2 mL, 29.5 mmol) at room temperature and the resulting mixture was heated at 50° C. and stirred for 45 min (oil bath). The reaction mixture was concentrated in vacuo to give 4.5 g of dark brown amorphous.

$^1$H-NMR (DMSO-$d_6$) δ 3.15 (m, 2H), 4.05 (m, 1H), 6.63 (dd, J=1.8, 8.7 Hz, 1H), 6.86 (d, J=2.1 Hz, 1H), 7.12 (d, J=2.1 Hz, 1H), 7.16 (d, J=9.0 Hz, 1H), 8.13 (br s, 3H), 10.73 (s, 1H), 13.8 (br s, 1H).

Mass(m/e)[M+H]$^+$221.

(Step 4)

To a solution of the compound (4) (4.64 g) which was synthesized in the above step without purification in 30 mL of acetone was added a solution of 3.1 g of $Na_2CO_3$ in 30 mL of water at ice-cooling. To the mixture was added 5-bromo-2-thiophene sulfonyl chloride (2.56 g, 9.79 mmol) and the resulting mixture was stirred for 40 min. The reaction mixture was pored into water (50 mL) and the resulting mixture was washed with diethylether (100 mL). After the aqueous layer was acidified with 2 mol/L HCl (30 mL), the layer was extracted with ethyl acetate (100 mL×2). The organic layer was washed with brine (50 mL×2), dried over $Na_2SO_4$, and concentrated in vacuo to give 2.8 g of dark brown amorphous. The residue was subjected to silica gel column chromatography and the fractions (including the compound (5)) eluted with $CHCl_3$—MeOH (100-1)–(10-1) were collected and concentrated in vacuo to give 0.72 g of dark yellow amorphous. A part of the amorphous was recrystallized from ethyl acetate (30 mg). The rest and the mother liquid was combined and concentrated in vacuo and the residue (0.67 g) was used the next step.

$^1$H-NMR (DMSO-$d_6$) δ 2.91 (m, 2H), 3.92 (m, 1H), 6.57 (dd, J=2.1, 8.4 Hz, 1H), 6.74 (d, J=2.1 Hz, 1H), 6.98 (d, J=2.4 Hz, 1H), 7.04 (d, J=3.9 Hz, 1H), 7.08 (d, J=3.9 Hz, 1H), 7.1 (d, J=8.4 Hz, 1H), 8.58 (br, 1H), 10.49 (s, 1H), 12.0–13.0 (1H).

[α]$_D$ −15.9±1.1 (28° C., 0.504%, DMSO).

IR cm$^{-1}$ (KBr) 3309, 1690, 1626, 1490, 1399, 1339, 1190, 1153.

HR-MS ($C_{15}H_{13}N_2O_5S_2Br$:444); [M−H]:
m/e443—$C_{15}H_{12}N_2O_5S_2{}^{79}Br$,
m/e445—$C_{15}H_{12}N_2O_5S_2{}^{81}Br$.

(Step 5)

The compound (5) (1.75 g) and p-tolylacetylene (0.91 g, 7.83 mmol) were dissolved in 17 mL of dry DMF and to the mixture were added $PdCl_2(PPh_3)_2$, CuI, and triethylamine. The reaction mixture was heated at 50° C. (oil bath) and stirred for 2 h. The resulting mixture was poured into water (100 mL) and washed with diethylether (50 mL). The organic layer was washed with water (100 mL×2), dried over $Na_2SO_4$, and concentrated in vacuo to give 2.1 g of dark brown paste. The obtained residue was subjected to silica gel column chromatography and the fractions eluted with $CHCl_3$—MeOH (100-1)–(25-1) were collected. The crystals (0.29 g) collected by the fractions were filtrated and the filtration was concentrated in vacuo to give 1.288 g of brown amorphous. Further, the amorphous was subjected to HPLC (Develosil 15/30; Φ50×500 mm; 50% $CH_3CN$ (0.2% AcOH); 254 nm; 70 mL/min) to give 0.81 g of pale brown crude crystals. The obtained crystals (0.29 g) and the crude crystals (0.81 g) were combined (1.1 g) and recrystallized from MeOH—$H_2O$ to yield compound (A-1) as pale brown needle crystals (864 mg, the purity was 98.6% detected by HPLC).

Mp. 200–202(dec).

$^1$H-NMR (DMSO-$d_6$) δ 2.46 (s, 3H), 2.81 (dd, J=6.0, 14.4 Hz, 1H), 3.01 (dd, J=6.0, 14.4 Hz, 1H), 3.98 (m, 1H), 6.57 (dd, J=1.8, 7.8 Hz, 1H), 6.75 (d, J=1.8 Hz, 1H), 6.70 (d, J=3.0 Hz, 1H), 7.10 (d, J=9.0 Hz, 1H), 7.16 (d, J=4.2 Hz, 1H), 7.22 (d, J=4.2 Hz, 1H), 7.28 (d, J=7.8 Hz, 2H), 7.49 (d, J=7.8 Hz, 2H), 8.62 (s, 1H), 8.63 (br, 1H), 10.53 (d, J=1.8 Hz, 1H), 12.79 (br, 1H).

IR cm$^{-1}$ (KBr) 3390, 3283, 2206, 1730, 1371, 1340, 1205, 1156.

[α]$_D$ +34.7±1.5 (27° C., 0.505%, DMSO).

Elemental analysis (%) $C_{24}H_{20}N_2O_5S_2 \cdot H_2O$
Calcd.: C, 57.84; H, 4.34; N, 5.47; S, 12.58.
Found: C, 57.82; H, 4.45; N, 5.62; S, 12.86.

Compound (A-2) to Compound (A-13) were synthesized in a manner similar to that described in Example 1. Their physical data were shown in Tables 1 to 3.

TABLE 1

| Example No. | Compound No. | Chemical Formula | $^1$H-NMR(DMSO-$d_6$) |
|---|---|---|---|
| 2 | A-2 | 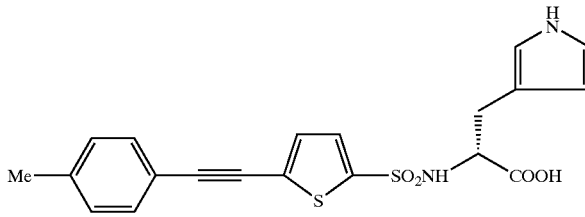 | 2.36(s, 3H), 2.89(dd, J=8.4, 14.4Hz, 1H), 3.08(dd, J=6.0, 14.4Hz, 1H), 3.98(m, 1H), 6.69 (dd, J=2.1, 9.0Hz, 1H), 6.91 (d, J=2.1Hz, 1H), 7.06(d, J=2.1Hz, 1H), 7.17(d, J=3.9Hz, 1H), 7.19(d, J=9.0Hz, 1H), 7.25(d, J=3.9Hz, 1H), 7.28(d, J=8.1Hz, 2H), 7.49(d, J=8.1Hz, 2H), 8.66(br s, 1H), 10.67 (s, 1H) |
| 3 | A-3 | 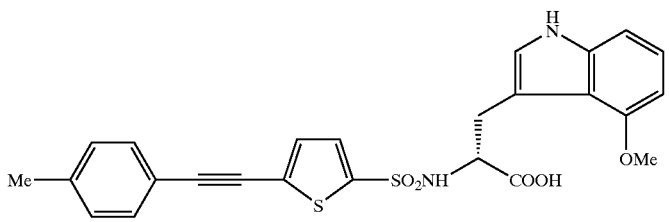 | 2.36(s, 3H), 2.90(dd, J=8.7, 13.8Hz, 1H), 3.19(dd, J=6.0, 13.8Hz, 1H), 3.79(s, 3H), 4.17 (br s, 1H), 6.40(d, J=6.9Hz, 1H), 6.8–7.0(m, 3H), 7.03(d, J=3.9Hz, 1H), 7.10(d, J=3.9Hz, 1H), 7.28(d, J=7.8Hz, 2H), 7.49(d, J=7.8Hz, 2H), 8.48 (br s, 1H), 10.74(s, 1H), 12.54 (br s, 1H) |
| 4 | A-4 | 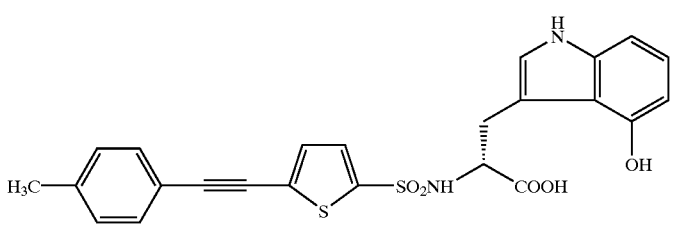 | 2.36(s, 3H), 2.91(dd, J=9.3, 13.8Hz, 1H), 3.22(dd, J=5.4, 13.8Hz, 1H), 4.28(br s, 1H), 6.29 (d, J=7.6Hz, 1H), 6.74(d, J=8.0Hz, 1H), 6.79(t, J=7.8Hz, 1H), 6.87(d, J=2.0Hz, 1H), 7.03(d, J=3.9Hz, 1H), 7.06 (d, J=3.9Hz, 1H), 7.28(d, J=8.0Hz, 2H), 7.48(d, J=8.0Hz, 2H), 8.52(s, 1H), 9.44(s, 1H), 10.61(d, J=2.0Hz,1H), 12.57(s, 1H) |
| 5 | A-5 | 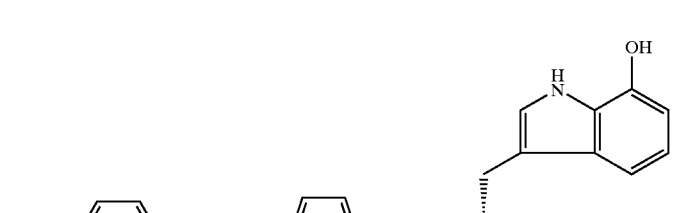 | 2.35(s, 3H), 2.87(dd, J=8.1, 14.5Hz, 1H), 3.06(dd, J=6.3, 14.5Hz, 1H), 4.00(q, J=7Hz, 1H), 6.48(d, J=7.4Hz, 1H), 6.76 (t, J=7.6Hz, 1H), 6.85(d, J=7.8Hz, 1H), 7.00(d, J=2.4Hz, 1H), 7.21(d, J=3.9Hz, 1H), 7.25(d, J=3.9Hz, 1H), 7.27 (d, J=8.1Hz, 2H), 7.49(d, J=8.1Hz, 2H), 8.69(d, J=8.7Hz, 1H), 9.47(s, 1H), 10.66(d, J=2.4Hz, 1H), 12.78(br s, 1H) |

TABLE 2

| Example No. | Compound No. | Chemical Formula | $^1$H-NMR(DMSO-$d_6$) |
|---|---|---|---|
| 6 | A-6 | 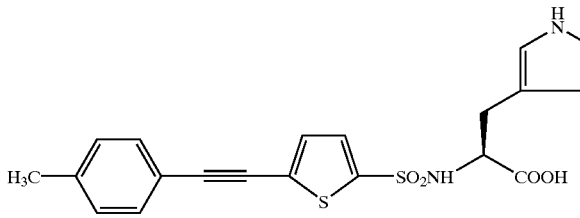 | 2.36(s, 3H), 2.89(dd, J=9.0, 14.7Hz, 1H), 3.09(dd, J=5.4, 14.7Hz, 1H), 3.97(br s, 1H), 6.88(dt, J=2.4, 9.0Hz, 1H), 7.1–7.3(m, 7H), 7.49(d, J=8.1Hz, 2H), 8.65(br s, 1H), 10.95(s, 1H), 12.85(br s, 1H) |

TABLE 2-continued

| Example No. | Compound No. | Chemical Formula | $^1$H-NMR(DMSO-$d_6$) |
|---|---|---|---|
| 7 | A-7 | | 2.8–3.0(m, 1H), 3.1–3.3(m, 1H), 3.78(s, 3H), 4.14(br s, 1H), 6.39(d, J=7.5Hz, 1H), 6.8–7.0(m, 5H), 8.44(br s, 1H), 10.72(s, 1H), 12.53(br s, 1H) |
| 8 | A-8 | | 2.90(dd, J=7.5, 14.7Hz, 1H), 2.96(s, 6H), 3.06(dd, J=6.6, 14.7Hz, 1H), 3.97(q, J=6.9Hz, 1H), 6.66(dd, J=2.4, 8.7Hz, 1H), 6.75(d, J=8.7Hz, 2H), 6.89(d, J=2.4Hz, 1H), 7.06(d, J=2.4Hz, 1H), 7.13(d, J=3.9Hz, 1H), 7.15(d, J=8.7Hz, 1H), 7.28(d, J=3.9Hz, 1H), 7.45(d, J=8.7Hz, 2H), 8.40(d, J=9.3Hz, 1H),10.66(s, 1H) 12.6(br s, 1H) |
| 9 | A-9 | | 1.97(m, 4H), 2.90(dd, J=8.1, 14.4Hz, 1H), 3.06(dd, J=5.4, 14.4Hz, 1H), 3.28(m, 4H), 3.93(m, 1H), 6.57(d, J=8.4Hz, 2H), 6.83(dt, J=2.7, 9.3Hz, 1H), 7.08(d, J=3.9Hz, 1H), 7.14(dd, J=2.7, 10.2Hz, 1H), 7.2–7.3(m, 2H), 7.24(d, J=3.9Hz, 1H), 7.42(d, J=8.4Hz, 2H), 8.36(br s, 1H), 10.93(s, 1H), 12.72(br s, 1H) |
| 10 | A-10 | | 1.97(m, 4H), 2.89(dd, J=7.5, 14.7Hz, 1H), 3.06(dd, J=6.3, 14.7Hz, 1H), 6.57(d, J=8.7Hz, 2H), 6.83(dt, J=2.4, 9.3Hz, 1H), 7.08(d, J=3.9Hz, 1H), 7.13(dd, J=2.4, 10.2Hz, 1H), 7.2–7.3(m, 2H), 7.24(d, J=3.9Hz, 1H), 7.42(d, J=8.7Hz, 2H), 8.38(d, J=8.7Hz, 1H), 10.94(s, 1H), 12.75(br s, 1H) |

TABLE 3

| Example No. | Compound No. | Chemical Formula | $^1$H-NMR(DMSO-$d_6$) |
|---|---|---|---|
| 11 | A-11 |  | 2.09(s, 3H), 2.86(dd, J=8.4, 14.4Hz, 1H), 3.04(dd, J=8.4, 14.1Hz, 1H), 3.91(m, 1H), 6.56(dd, J=2.4, 9.0Hz, 1H), 6.83(d, J=2.4Hz, 1H), 7.04(d, J=2.1Hz, 1H), 7.06(d, J=9.0Hz, 1H), 7.25(d, J=9.0Hz, 2H), 7.71(d, J=9.0Hz, 2H), 8.08(d, J=9.0Hz, 2H), 8.11(d, J=9.0Hz, 2H), 8.39(br s, 1H), 10.60(s, 1H),12.66(br s, 1H) |

TABLE 3-continued

| Example No. | Compound No. | Chemical Formula | $^1$H-NMR(DMSO-$d_6$) |
|---|---|---|---|
| 12 | A-12 | [structure: phenyl-tetrazole-phenyl-SO$_2$NH-CH(COOH)-CH$_2$-(5-fluoroindole)] | 2.85(dd, J=9.0, 14.4Hz, 1H), 3.05(dd, J=5.4, 14.4Hz, 1H), 3.93(m, 1H), 6.72(dt, J=2.7, 9.0Hz, 1H), 7.0–7.2(m, 3H), 7.6–7.8(m, 5H), 8.07(d, J=8.4Hz, 2H), 8.21(d, J=8.1Hz, 2H), 8.45(d, J=8.7Hz, 1H), 10.87 (s, 1H), 12.79(br s, 1H) |
| 13 | A-13 | [structure: 4-fluorophenyl-oxadiazole-phenyl-SO$_2$NH-CH(COOH)-CH$_2$-(5-fluoroindole)] | 2.83(dd, J=8.1, 14.4Hz, 1H) 3.04(dd, J=4.5, 14.4Hz, 1H), 3.91(m, 1H), 6.71(t, J=9.3Hz, 1H), 7.0–7.2(m, 3H), 7.54(t, J=8.7Hz, 2H), 7.63(d, J=8.4 Hz, 2H), 7.97(d, J=8, 4Hz, 2H), 8.25(t, J=6.3Hz, 2H), 8.47 (br s, 1H), 10.85(s, 1H), 12.86 (br s, 1H) |

TEST EXAMPLE

Test Example 1

Isolation and Purification of MMP-9

MMP-9 was purified by using a combination of procedures described in the method descrived in Y. Okada et al. (Yasunori Okada, Yukio Gonoji, Katsumi Naka, Katsuro Tomita, Isao Nakanishi, Kazushi Iwata and Taro Hayakawa: Matrix metalloproteinase 9 (92-kDa gelatinase/type IV collagenase) from HT1080 human fibrosarcoma cells. Purification and activation of the precursor and enzymic properties. J. Biol. Chem., 267 (1992) 21712–21719 and the other method (1) Yasunori Okada, Tatsuhisa Morodomi, Jan J, Enghild, Ko Suzuki, Atsushi Yasui, Isao Nakanishi, Guy Salvesen and Hideaki Nagase: Matrix metalloproteinase 2 from human rheumatoid synovial fibroblasts. Purification and activation of the precursor and enzymic properties. Eur. J. Biochem. 194 (1990) 721–730 or (2) Robin V Ward, Rosalind M Hembry, John J Reynolds and Gillian Murphy: The purification of tissue inhibitor of metalloproteinase-2 from its 72 kDa progelatinase complex. Biochem. J. 278 (1991) 179–187. Briefly, human fibrosarcoma ATCC HT1080 cell line was cultured to confluent in Dulbecco's Modified Medium (DMEM) containing 10% fetal-calf serum (FCS) at 37° C. for 48 hours (5%). Further, Confluent Cell was cultured in DMEM removed FCS (2nd). To obtain MMP-9, Phorbol-12-myristate-13-acetate (TPA) was added to this DMEM medium at a concentration of 50 ng/ml. The TPA treated medium was centrifuged at 3000 rpm for 15 min and the supernatant was concentrated to 450 ml by a Toyo-Roshi UP-20 apparatus with an ultrafiltration membrane. Then, this concentrated solution was purified by Gelatin-Sepharose and Concanavalin A-Sepharose. The pool containing MMP-9 was dialyzed, concentrated (Toyo-Roshi UP-20) and applied to columns of Sephacryl S-200 and Green A matrix for the separation from TIMP. The obtained Procollagenase was activated by TPCK-Trypsin (final conc. 3 µg/µl reaction mix.) for the assay.

Test Example 2

Isolation and Purification of MMP-2

MMP-2 was purchased from Calbiochem-Novabiochem International, Inc.

Test Example 3

Assay for Inhibitory Activities on each MMP

The enzymatic activity on each MMP was analyzed by the method described in "C Graham Knight, Frances Willenbrock and Gillian Murphy: A novel coumarin-labelled peptide for sensitive continuous assays of the matrix metalloproteinases: FEBS LETT., 296, (1992), 263–266". The substrate: MOCAc-Pro-Leu-Gly-Leu-A$_2$Pr(DNP)-Ala-Arg-NH$_2$ was purchased from Peptide Institute, Inc., Osaka, Japan.

The measurement of the inhibitory activities of a compound (inhibitor) was carried out by the following four methods;

A) Reaction with substrate, enzyme (MMPs) and inhibitor

B) Reaction with substrate and inhibitor, without enzyme

C) Reaction with substrate and enzyme (MMPs), without inhibitor

D) Reaction with substrate only

Each fluorescence values of above four methods was measured and % inhibition was calculated by using the following formula.

% inhibition=$\{1-(A-B)/(C-D)\} \times 100$

IC$_{50}$ means the concentration required to inhibit 50% of the enzyme activity.

The results are shown in Table 4.

TABLE 4

| Compound No. | IC$_{50}$ (MMP-2, µM) | IC$_{50}$ (MMP-9, µM) |
|---|---|---|
| A-1 | 0.000223 | 0.00244 |
| A-2 | 0.0106 | 0.0156 |
| A-3 | 0.0228 | 0.174 |
| A-4 | 0.000768 | 0.0243 |
| A-5 | 0.00121 | 0.00649 |
| A-6 | 0.0908 | 0.848 |
| A-8 | 0.000617 | 0.00666 |
| A-9 | 0.000137 | 0.000534 |

TABLE 4-continued

| Compound No. | IC$_{50}$ (MMP-2, $\mu$M) | IC$_{50}$ (MMP-9, $\mu$M) |
|---|---|---|
| A-10 | 0.00404 | 0.012 |
| A-11 | 0.00577 | 0.0160 |
| A-12 | 0.0858 | 1.42 |

FORMULATION EXAMPLE

Formulation Example 1

Granules are prepared using the following ingredients.

| Ingredients | The compound represented by the formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | The compound represented by the formula (I) | 10 mg |
|---|---|---|
| | Lactose | 79 mg |
| | Corn starch | 10 mg |
| | Magnesium stearate | 1 mg |
| | | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | The compound represented by the formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | The compound represented by the formula (I) | 10 mg |
|---|---|---|
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

INDUSTRIAL APPLICABILITY

The sulfonamide derivatives of the present invention have an inhibitory activities of the metalloproteinase and are useful as the treating or preventing agent of cancer, nephritis, osteoarthrosis, heart failure, autoimmune disease, and the like.

What is claimed is:

1. A compound of the formula (I):

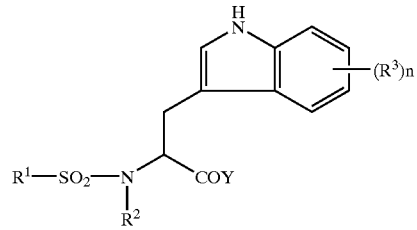

wherein $R^2$ is hydrogen, optionally substituted lower alkyl, or optionally substituted aralkyl;

$R^3$ is halogen, hydroxy, lower alkyloxy, or lower alkylthio;

n is an integer from 1 to 3;

$R^1$ is represented by the formula:

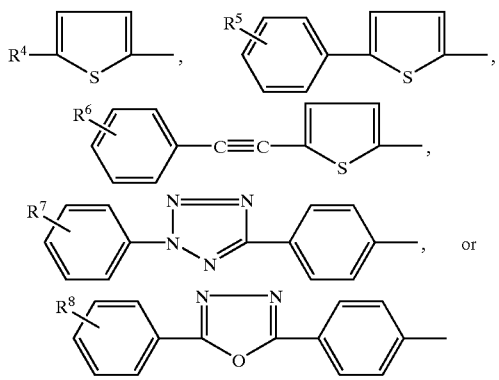

wherein $R^4$ is hydrogen, halogen, optionally substituted lower alkyl, lower alkyloxy, lower alkylthio, optionally substituted amino, or nitro;

$R^5$ is hydrogen, halogen, optionally substituted lower alkyl, lower alkyloxy, lower alkylthio, optionally substituted amino, nitro, or a non-aromatic heterocyclic group, provided that when R⁵ is amino substituted with two lower alkyls, R³ is not 6-methyloxy or 5-fluoro;

R⁶ is hydrogen, halogen, optionally substituted lower alkyl, lower alkyloxy, lower alkylthio, optionally substituted amino, or nitro, provided that when R⁶ is lower alkyl, R³ is not 6-hydroxy or 6-lower alkyloxy;

R⁷ is halogen, optionally substituted lower alkyl, lower alkyloxy, lower alkylthio, optionally substituted amino, or nitro;

R⁸ is hydrogen, halogen, optionally substituted lower alkyl, lower alkyloxy, lower alkylthio, optionally substituted amino, or nitro; and Y is —OH or —NHOH, its optically active substance, its prodrug, its pharmaceutically acceptable salt, or its solvate.

2. A compound of claim 1, wherein R¹ is a group represented by the formula:

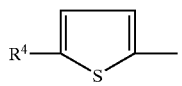

wherein R⁴ is halogen, its optically active substance, its prodrug, its pharmaceutically acceptable salt, or its solvate.

3. A compound of claim 1, wherein R¹ is a group represented by the formula:

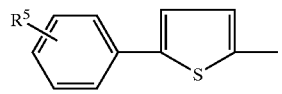

wherein R⁵ is optionally substituted amino or a non-aromatic heterocyclic group, provided that when R⁵ is amino substituted with two lower alkyls, R³ is not 6-methyloxy or 5-fluoro;

its optically active substance, its prodrug, its pharmaceutically acceptable salt, or its solvate.

4. A compound of claim 1, wherein R¹ is a group represented by the formula:

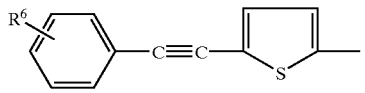

wherein R⁶ is a lower alkyl, its optically active substance, its prodrug, its pharmaceutically acceptable salt, or its solvate.

5. A compound of claim 1, wherein R¹ is a group represented by the formula:

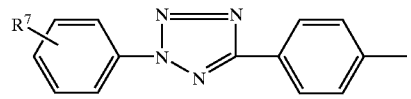

wherein R⁷ is lower alkyloxy, its optically active substance, its prodrug, its pharmaceutically acceptable salt, or its solvate.

6. A compound of claim 1, wherein R¹ is a group represented by the formula:

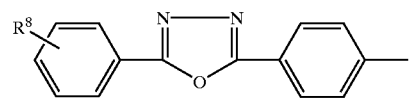

wherein R⁸ is halogen, its optically active substance, its prodrug, its pharmaceutically acceptable salt, or its solvate.

7. A compound of any one of claims 1 to 6, wherein R² is hydrogen, its optically active substance, its prodrug, its pharmaceutically acceptable salt, or its solvate.

8. A compound of any one of claims 1 to 6, wherein R³ is halogen, hydroxy, or lower alkyloxy and n is 1, its optically active substance, its prodrug, its pharmaceutically acceptable salt, or its solvate.

9. A pharmaceutical composition containing a compound of any one of claims 1 to 6 as an active ingredient.

10. A method for treating a disease related with matrix metalloproteinase of a mammal, which comprises administration to said mammal of a compound of any one of claims 1 to 6 in a pharmaceutically effective amount.

11. The compound of claim 1 wherein the non-aromatic heterocyclic group is pyrrolidinyl.

12. A compound of the formula (I):

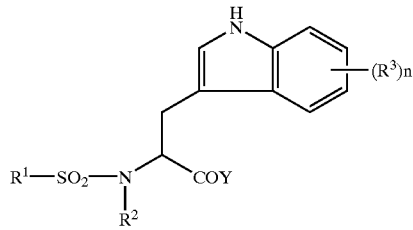

wherein R² is hydrogen, optionally substituted lower alkyl, or optionally substituted aralkyl;

R³ is halogen, hydroxy, lower alkyloxy, or lower alkylthio;

n is an integer from 1 to 3;

R¹ is represented by the formula:

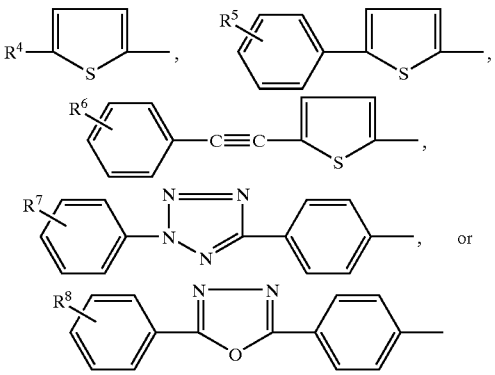

wherein

R⁴ is hydrogen, halogen, optionally substituted lower alkyl, lower alkyloxy, lower alkylthio, optionally substituted amino, or nitro;

R⁵ is hydrogen, halogen, optionally substituted lower alkyl, lower alkyloxy, lower alkylthio, optionally substituted amino, nitro, provided that when R⁵ is amino substituted with two lower alkyls, R³ is not 6-methyloxy or 5-fluoro;

R⁶ is hydrogen, halogen, optionally substituted lower alkyl, lower alkyloxy, lower alkylthio, optionally substituted amino, or nitro, provided that when R⁶ is lower alkyl, R³ is not 6-hydroxy or 6-lower alkyloxy;

R⁷ is halogen, optionally substituted lower alkyl, lower alkyloxy, lower alkylthio, optionally substituted amino, or nitro;

R⁸ is hydrogen, halogen, optionally substituted lower alkyl, lower alkyloxy, lower alkylthio, optionally substituted amino, or nitro; and Y is —OH or —NHOH, its optically active substance, its prodrug, its pharmaceutically acceptable salt, or its solvate.

13. A compound of formula A1:

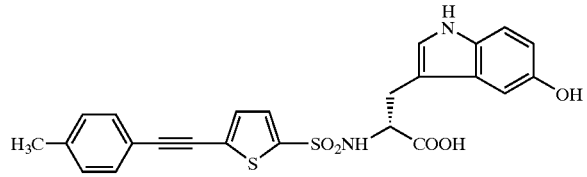

A-1 its optically active substance, its prodrug, its pharmaceutically acceptable salt, or its solvate.

* * * * *